United States Patent
Hayakawa

(10) Patent No.: US 10,105,459 B2
(45) Date of Patent: Oct. 23, 2018

(54) METHOD AND APPARATUS FOR STERILIZING CONTAINER

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Shinjuku-Ku (JP)

(*) Notice: Subject to any disclaimer, the term of this patent is extended or adjusted under 35 U.S.C. 154(b) by 0 days.

(21) Appl. No.: 15/117,526

(22) PCT Filed: Mar. 13, 2015

(86) PCT No.: PCT/JP2015/057437
§ 371 (c)(1),
(2) Date: Aug. 9, 2016

(87) PCT Pub. No.: WO2015/137480
PCT Pub. Date: Sep. 17, 2015

(65) Prior Publication Data
US 2016/0375160 A1    Dec. 29, 2016

(30) Foreign Application Priority Data

Mar. 14, 2014  (JP) .................. 2014-051122

(51) Int. Cl.
*A61L 2/04* (2006.01)
*A61L 2/20* (2006.01)
(Continued)

(52) U.S. Cl.
CPC .................. *A61L 2/04* (2013.01); *A61L 2/186* (2013.01); *A61L 2/208* (2013.01); *A61L 2/22* (2013.01);
(Continued)

(58) Field of Classification Search
CPC .................. A61L 2/04; A61L 2/208
See application file for complete search history.

(56) References Cited

U.S. PATENT DOCUMENTS

2008/0107562 A1* 5/2008 Hayashi ............... A61L 2/06
422/28
2010/0170867 A1  7/2010 Hayakawa
(Continued)

FOREIGN PATENT DOCUMENTS

| CN | 103261033 A | 8/2013 |
| EP | 2 653 395 A1 | 10/2013 |

(Continued)

OTHER PUBLICATIONS

English Translation of Publication No. WO 2012081489 A1 provided by Espacenet.com: Hayakawa, Atsushi; Beverage Filling Method and Machine; Jun. 21, 2012 (Year: 2012).*

(Continued)

*Primary Examiner* — Kevin Joyner
(74) *Attorney, Agent, or Firm* — Burr & Brown, PLLC

(57) ABSTRACT

Inner and outer surfaces of a container which is filled with drink are sterilized. A sterilizer is applied to an outer surface of a container by blasting the sterilizer toward the outer surface of the container from at least one nozzle for sterilizer disposed so as not to intersect with a mouth portion of the container, an inner surface of the container is sterilized by heat of a hot-water supplied into the container from a nozzle for hot-water, and the sterilizer adhering to the outer surface of the container is activated with the heat transferred from the hot-water to thereby sterilize the outer surface of the container.

7 Claims, 7 Drawing Sheets

(51) Int. Cl.
  *B67C 7/00* (2006.01)
  *A61L 2/18* (2006.01)
  *A61L 2/22* (2006.01)
  *A61L 2/26* (2006.01)
  *B67C 3/22* (2006.01)

(52) U.S. Cl.
  CPC ............. *A61L 2/26* (2013.01); *B67C 7/0073* (2013.01); *A61L 2202/15* (2013.01); *A61L 2202/23* (2013.01); *B67C 2003/227* (2013.01)

(56) References Cited

U.S. PATENT DOCUMENTS

| | | |
|---|---|---|
| 2011/0094616 A1 | 4/2011 | Hayakawa et al. |
| 2014/0144105 A1 | 5/2014 | Hayakawa et al. |

FOREIGN PATENT DOCUMENTS

| | | | | |
|---|---|---|---|---|
| EP | 3 069 846 A1 | 9/2016 | | |
| JP | 03-212333 A1 | 9/1991 | | |
| JP | 05-338629 A1 | 12/1993 | | |
| JP | 07-033123 A1 | 2/1995 | | |
| JP | 2004-299722 A1 | 10/2004 | | |
| JP | 2006-069672 A1 | 3/2006 | | |
| JP | 2006-160373 A1 | 6/2006 | | |
| JP | 2009-269677 A1 | 11/2009 | | |
| JP | 2009-280222 A1 | 12/2009 | | |
| JP | 2010-042864 A1 | 2/2010 | | |
| JP | 2010-047321 A1 | 3/2010 | | |
| JP | 2012-126436 A1 | 7/2012 | | |
| JP | 2013-203453 A1 | 10/2013 | | |
| JP | 2013-224183 A1 | 10/2013 | | |
| WO | WO-2012081489 A1 | * | 6/2012 | ........... B67C 7/0073 |
| WO | 2013/021882 A1 | 2/2013 | | |

OTHER PUBLICATIONS

International Search Report and Written Opinion (Application No. PCT/JP2015/057437) dated Jun. 9, 2015.

Chinese Office Action (with English translation), Chinese Application No. 201580006790.7, dated May 16, 2017 (17 pages).

Extended European Search Report (Application No. 15762072.5) dated Oct. 6, 2017.

Chinese Office Action (with English translation), Chinese Application No. 201580006790.7, dated Jan. 31, 2018.

* cited by examiner

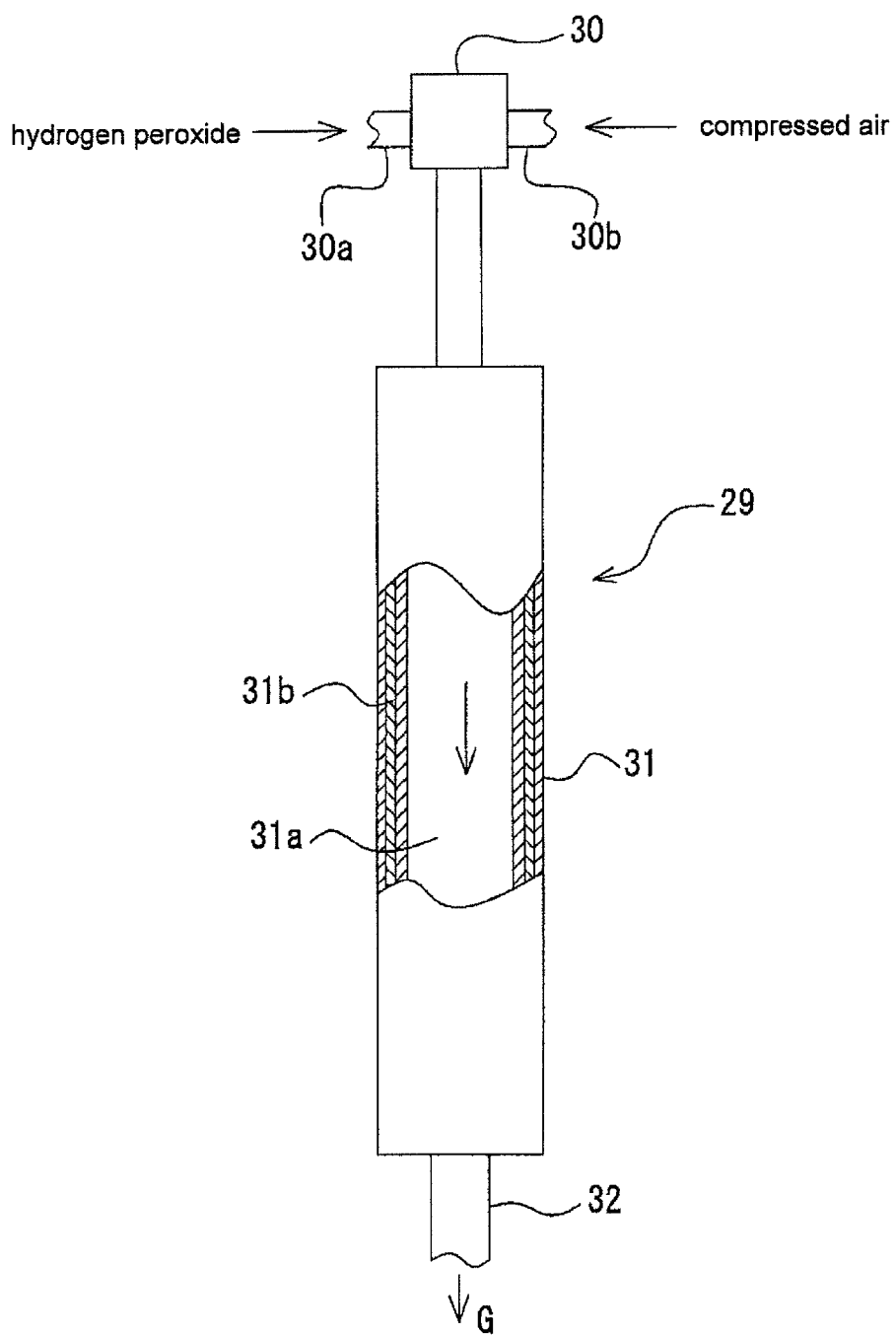

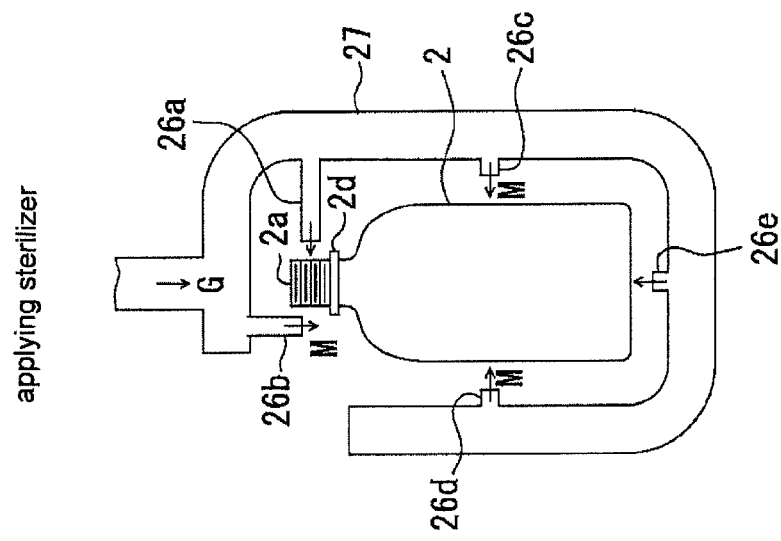
FIG.4(C) applying sterilizer
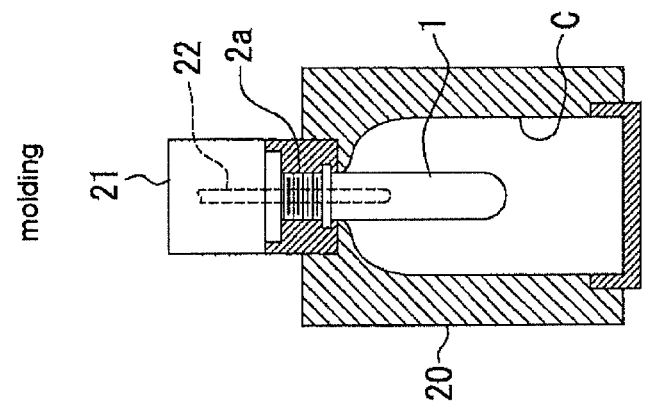
FIG.4(B) molding
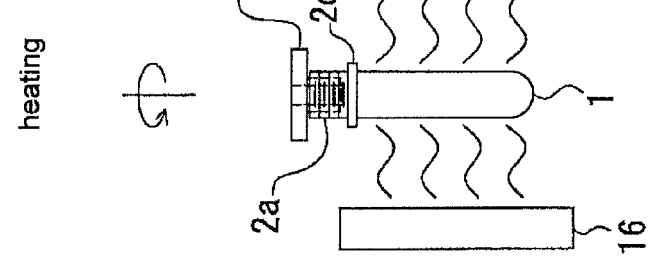
FIG.4(A) heating

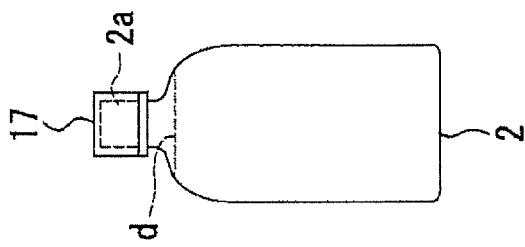
FIG.5(D) hot-water rinsing
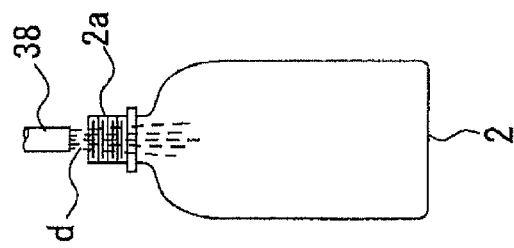
FIG.5(E) filling drink
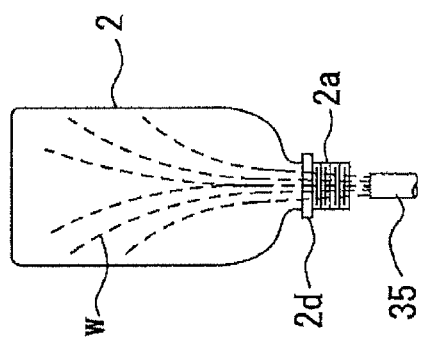
FIG.5(F) sealing

METHOD AND APPARATUS FOR STERILIZING CONTAINER

BACKGROUND OF THE INVENTION

Field of the Invention

The present invention relates to method and apparatus for sterilizing a container.

Description of Related Art

In a conventional technology, when a drink-filled container that is filled with drink such as mineral water, carbonated water or like drink and then sealed, is manufactured, the container is subjected to sterilizing treatment before the filling of the drink (for example, refer to Patent Documents 1-8).

Such sterilizing treatment is generally performed by supplying a sterilizer (sterilizing agent) such as peracetic acid series sterilizer, slight-acidic hypochlorite water, or like sterilizer into the container (for example, refer to Patent Documents 1-4).

Furthermore, there has been tried to sterilize the container only with hot water without using any sterilizer (for example, refer to Patent Documents 5-8).

PRIOR ART DOCUMENT

Patent Document

Patent Document 1: Japanese Patent Laid-open Publication No. 2006-69672
Patent Document 2: Japanese Patent Laid-open Publication No. 2010-42864
Patent Document 3: Japanese Patent Laid-open Publication No. 2010-47321
Patent Document 4: Japanese Patent Laid-open Publication No. 2013-203453
Patent Document 5: Japanese Patent Laid-open Publication No. HEI 5-338629
Patent Document 6: Japanese Patent Laid-open Publication No. 2004-299722
Patent Document 7: Japanese Patent Laid-open Publication No. 2006-160373
Patent Document 8: Japanese Patent Laid-open Publication No. 2009-269677

SUMMARY OF THE INVENTION

Problem to be Solved by the Invention

In the conventional container sterilizing method using a sterilizer provides a problem such that the sterilizer likely remains inside the container. Particularly, in a case where an inner content filling the container is one such as drink water including no component other than water, there is much fear that hydrogen peroxide contained in the sterilizer is not decomposed and remains in the drink water.

On the other hand, in the method of sterilizing the container with the hot water without using any sterilizer, when the hot water is blasted to the inner and outer surfaces of the container for sterilizing the surfaces, there is a fear of excessively increasing temperature of the container, which may result in deformation of the container.

Moreover, because hot water to be used for the sterilization of the container is limited to a sterilized water (aseptic water) water, if the hot water is used for the sterilization of the outer surface of the container in addition to the inner surface thereof, cost for installation of facility increases, as well as running cost for manufacturing of steam, aseptic water and the like, thus providing inconvenience.

Accordingly, the present invention has an object to solve such problems and inconveniences mentioned above.

Means for Solving the Problem

In order to solve the above problems, the present invention adopts the following structure.

It is further to be noted that although the description is made with parentheses to reference numerals for easy understanding of the invention, the present invention is not limited thereto.

That is, the present invention according to a first aspect adopts a method of sterilizing a container, wherein a sterilizer is applied to an outer surface of a container (2) by blasting the sterilizer toward the outer surface of the container (2) from at least one nozzle (26a to 26d) for sterilizer disposed so as not to intersect with a mouth portion (2a) of the container (2), an inner surface of the container (2) is sterilized by heat of a hot-water (w) supplied into the container from a nozzle (35) for hot-water, and the sterilizer adhering to the outer surface of the container (2) is activated with the heat transferred from the hot-water (w) to thereby sterilize the outer surface of the container (2).

According to a second aspect of the present invention, it may be desired that, in the container sterilizing method according to the first aspect, at least one sterilizer nozzle is provided so as to extend along the outer surface of a cylindrical wall portion of the mouth portion of the container.

According to a third aspect of the present invention, it may be desired that, in the container sterilizing method according to the first aspect, at least one sterilizer nozzle is provided so as to intersect with a cylindrical wall portion of a mouth portion of the container.

According a fourth aspect of present invention, it may be desired that, in the container sterilizing method according to any one of the first to third aspects, a conduit is arranged so as to extend to surround a contour of the container in a flat plane including an axis of the container, and the sterilizer nozzle is provided for the conduit in a manner such that the sterilizer introduced into the conduit is discharged toward the outer surface of the container from the sterilizer nozzle.

According to a fifth aspect of the present invention, it may be desired that, in the container sterilizing method according to any one of the first to fourth aspect, the sterilizer in form of gas is changed to sterilizer mist by discharging the sterilizer gas through the sterilizer nozzle.

According to a sixth aspect of the present invention, it may be desired that, in the container sterilizing method according any one of the first to fifth aspects, the sterilizer gas is blasted to the container to which heat at a time of molding process remains.

The present invention according to a seventh aspect adopts an apparatus for sterilizing a container, wherein a conveying means for conveying a container (2) is provided, a sterilizer is discharged toward an outer surface of the container (2) from an upstream side to a downstream side with respect to the conveying means, at least one sterilizer nozzle (26a to 26d) for applying the sterilizer to an outer surface of the container (2) and a nozzle (35) for hot-water (w) for supplying the hot water (w) into the container (2) are disposed subsequently, an inner surface of the container (2)

is sterilized by heat of the hot-water (w) supplied into the container from the nozzle (35) for hot-water (w), and the sterilizer adhering to the outer surface of the container (2) is activated with the heat transferred from the hot-water (w) to thereby sterilize the outer surface of the container (2).

According to an eight aspect of the present invention, it may be desired that, in the container sterilizing apparatus according to the seventh aspect, at least one sterilizer nozzle is provided so as to extend along the outer surface of a cylindrical wall portion of the mouth portion of the container.

According to a ninth aspect of the present invention, it may be desired that, in the container sterilizing apparatus according to the seventh aspect, at least one sterilizer nozzle is provided so as to intersect with a cylindrical wall portion of a mouth portion of the container.

According to a tenth aspect of the present invention, it may be desired that, in the container sterilizing apparatus according to any one of the seventh to ninth aspects, a conduit (27) is arranged so as to extend to surround a contour of the container in a flat plane including an axis of the container (2), and the sterilizer nozzle (26a to 26d) is provided for the conduit in a manner such that the sterilizer introduced into the conduit (27) is discharged toward the outer surface of the container (2) from the sterilizer nozzle (35).

According to an eleventh aspect of the present invention, it may be desired that, in the container sterilizing apparatus according to any one of the seventh to tenth aspects, the sterilizer in form of gas is changed to sterilizer mist by discharging the sterilizer gas through the sterilizer nozzle.

According to a twelfth aspect of the present invention, it may be desired that, in the container sterilizing apparatus according to any one of the seventh to eleventh aspects, the sterilizer gas is blasted to the container to which heat at a time of molding process remains.

Effect of the Invention

According to the present invention, since the inner surface of the container (2) can be sterilized by the hot-water (w) without using a sterilizer, the sterilizer does not remain in the container (2). Accordingly, a drink can fill the container (2) even if the drink is difficult to decompose hydrogen peroxide of a carbonated water. Furthermore, since the sterilizer is applied only to the outer surface of the container (2) and the sterilizer supplied into the container (2) can be activated by the heat from the hot-water (w) fed into the container (2), the sterilizing effect to the outer surface of the container (2) can be enhanced. Therefore, it becomes possible to properly prevent bacteria or like substance adhering to the outer surface of the container (2) from entering the aseptic chamber (9) which is required to have a high aseptic condition. In addition, even if extremely small amount of sterilizer enters the container (2), the sterilizer is discharged out of the container (2) by the hot-water (w) fed into the container (2), so that there is no fear that the sterilizer remains in the container (2).

BRIEF DESCRIPTION OF THE DRAWINGS

FIG. 3 is a vertical sectional view showing an evaporator.

FIGS. 4(A), (B) and (C) represent steps respectively of a preform heating step, a bottle molding step, and sterilizer supplying step during the manufacture of a drink-filled product.

FIGS. 5(D), (E) and (F) represent steps respectively of a hot-water rinsing step, a drink filling step, and a sealing step in the drink-filled product manufacturing process.

EMBODIMENT FOR CARRYING OUT THE INVENTION

Hereunder, an embodiment for carrying out the present invention will be described.

First Embodiment

Figure 1:
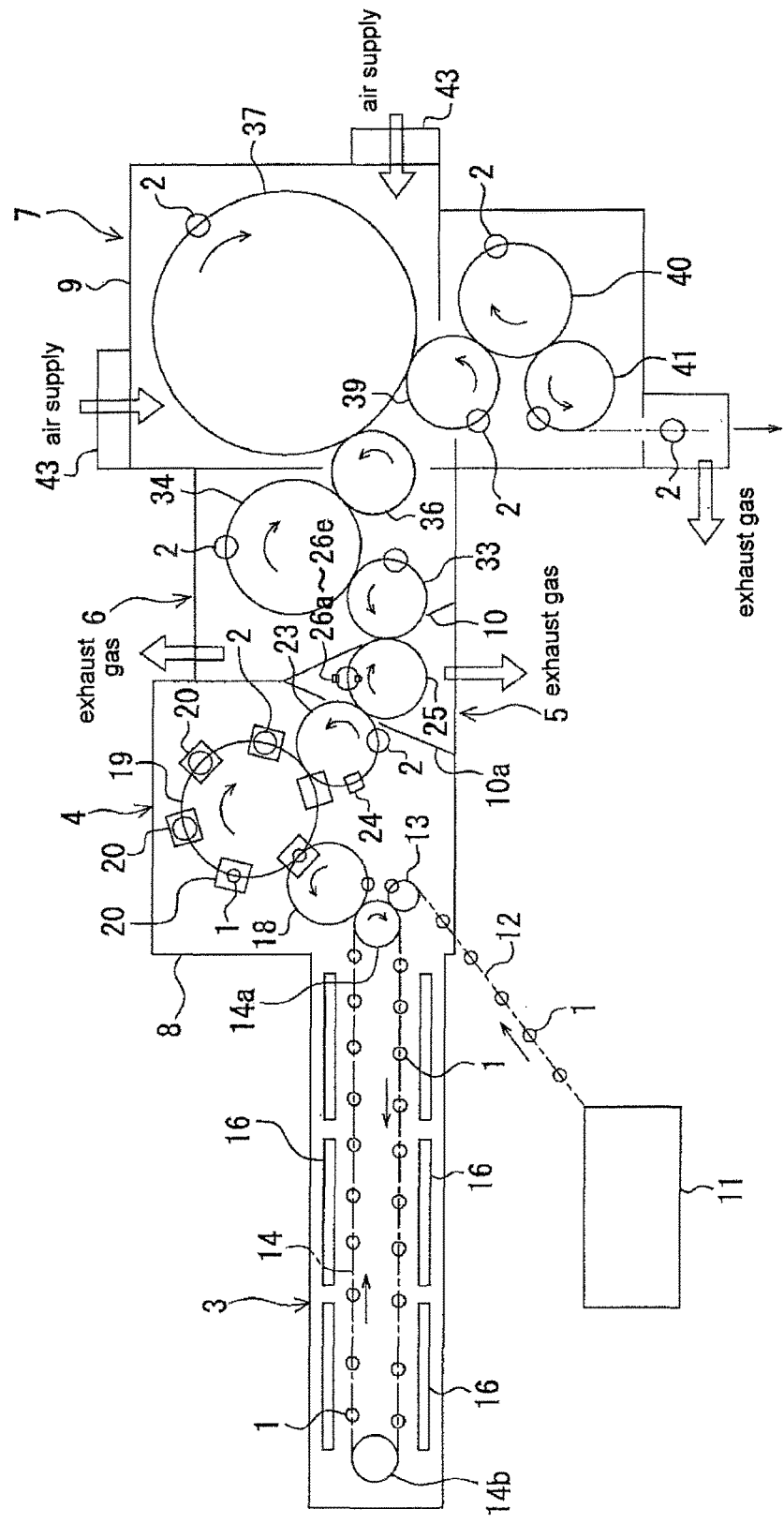
FIG. 1 is a plan view schematically illustrating an aseptic filling system incorporated with a sterilizing device for a container according to the present invention.

A sterilizing device for a container is, as shown in FIG. 1, incorporated into an aseptic filling system for producing a drink-filled product, in which a bottle 2 is molded (see FIG. 4(C)) as a container from a bottomed preform 1 (see FIG. 4(A)), the bottle 2 is sterilized, is filled up with drink such as mineral water, carbonated water or like, and then sealed, thereby producing a drink-filled product.

Within the aseptic filling system, there is provided a conveying means for conveying the preforms 1 and the bottles 2 from the preform supply process to the product completing process.

Furthermore, within the aseptic filling system, there are provided, in series, a heating section 3 for heating the preform 1 to a temperature suitable for a blow-molding process, a molding section 4 for molding the preform 1 into the bottle 2 by blowing air (air-blowing process), a sterilizer supplying section 5 for applying a sterilizer to an outer surface of the bottle 2, a hot-water rinsing section 6 for supplying hot water into the bottle 2, and a filling section in which the drink fills the bottle 2, which is then sealed as a drink-filled product.

A portion extending from the heating section 3 to the molding section 4 is covered by a cover 8, and a portion extending from the sterilizer supplying section 5 to the filling section 7 are covered by an aseptic chamber 9. Moreover, the sterilizer supplying section 5, in the aseptic chamber 9, is surrounded by a partition wall 10 so as not to disperse the sterilizer to its surrounding.

A preform supply machine 11 for subsequently supplying the preforms 1 at a predetermined interval is provided on an upstream side of the heating section 3.

The preform 1 is produced, as shown in FIG. 4(A) by using a test-tube shape bottomed substance, for example, PET (polyethylene-terephthalate), through an injection molding process at a portion outside the aseptic filing system. The preform 1 is molded into the bottle 2, as a container by the blow-molding process, with a mouth portion 2a, and a male thread portion formed and a support ring 2d around the mouth portion 2a. However, these portions are also formed at an initial stage of molding the preform 1.

A conveyer chute 12 as preform carry-in means is provided so as to extend from the preform supply machine 11 to the heating section 3.

The conveyer chute 12 extends into the heating section 3, and a wheel 13 is connected to the terminal end thereof.

Grippers and like means, not shown, are provided for the conveyer chute 12 and the wheel 13 with the preforms 1 being held during the conveyance thereof.

The heating section 3 has a furnace chamber extending in one direction, and an endless chain 14 is stretched in the furnace chamber, as preform conveying means, between a pair of pulleys 14a and 14a opposed to each other, and the conveying chute 12 is connected on one of the pulleys 14a disposed on an inlet side of the furnace chamber.

A number of holding members 15 for holding the preforms 1 such as shown in FIG. 4(A) are mounted to the endless chain 14 at a predetermined pitch, and each of the preform holding members 15 rotates while travelling together with the endless chain 14.

As shown in FIG. 4(A), the holding member 15 is inserted into the preform 1 from the mouth portion 2a of the preform 1 transferred to the endless chain 14 from the wheel 13, and the preform 1 is then held by the holding member 15 in the positive standing attitude.

Heaters 16 radiating infrared rays are mounted to the inner wall surface of the furnace chamber of the heating section 3 so as to be along outward and return paths of the endless chain 14.

The preform 1 is received by the holding member 15 through the conveying chute 12 and the wheel 13, and then travels along the inner wall surface of the heating section 3 while rotating. The preform conveyed with the holding member 15 is heated by the heaters 16 extending on the inner wall surface of the heater. The preform 1 rotates together with the rotation of the holding member 15 during the travelling in the heating section 3, and is evenly heated by the heaters 16 to the temperature of 90 to 130° C. suitable for the blow-molding process for the preform except the mouth portion 2a of the preform 1. The mouth portion 2a is heated to a temperature less than 70° C. to prevent the bottle 2 from being deformed and damaged in the sealing performance when the cap 17 (see FIG. 5(F)) is applied to the mouth portion 2a.

A train of wheels 18 and 19 for receiving the preform 1 heated by the heater 16 and conveying the preform 1 into the molding section 4 are disposed to a portion contacting the return path of the endless chain 14 in one of the pulleys 14a thereof.

Around the upstream side wheel 18 among these wheels, is provided with a gripper, not shown, for conveying the preform 1 with the mouth portion 2a thereof being held and conveying the preform 1 to the downstream side wheel 19.

On the other hand, around the downstream side wheel 19, are provided a plurality of blow-molding molds 20, each of which is splittable into two-parts, and which receives the heated preform 1 from the gripper of the upstream side wheel 18 and molds the preform 1 into the bottle 2 by blowing air (i.e., by blow-air). Each of the molds 20 is turned at a constant speed together with the rotation of the wheel 19.

A valve block 21 is detachably connected to each of the blow-molding molds 20 as shown in FIG. 4(B). The valve block 21 is one for mainly controlling the supply and exhaust of the blowing-air, and an extension rod is disposed within the valve block 21 to be vertically slidable.

When the blow-molding mold 20 receives the heated preform 1 from the wheel 18 side, both the mold parts (halves) are closed and the preform 1 is molded into the bottle 2 while rotating together with the valve block 21. In the blow-molding process, the extension rod 22 is lowered into the valve block 21, and when the extension rod 22 abuts against the inner bottom portion of the preform 1, the preform 1 is extended, and thereafter, the aseptic blow-air is blasted into the preform 1 through a nozzle, not shown, provided for the valve block 21. In this operation, since the preform 1 is heated to the predetermined temperature in the heating section 3, the preform 1 can be smoothly blow-molded into the bottle 2.

The blow-molding mold 20 is turned together with the wheel 19, is opened at an instance of contacting the downstream side conveying wheel 23, and the molded bottle 2 is then released from the mold 20. The thus molded bottle 2 is received by a gripper, not shown, of the conveying wheel 23.

An inspection camera 24 is provided as occasion demands for a predetermined portion around the conveying wheel 23, for example, for inspecting condition (i.e., right or wrong, or good or defective) of smoothness or flatness of an end face of the mouth portion 2a of the bottle 2.

Another wheel 25 as bottle conveying means is connected to the conveying wheel 23, and around this wheel 25, a gripper for gripping the mouth portion 2a of the bottle 2 is disposed.

As shown in FIG. 1, the downstream side from the wheel 25 is covered by the aseptic chamber 9 described hereinbefore.

Figure 2:
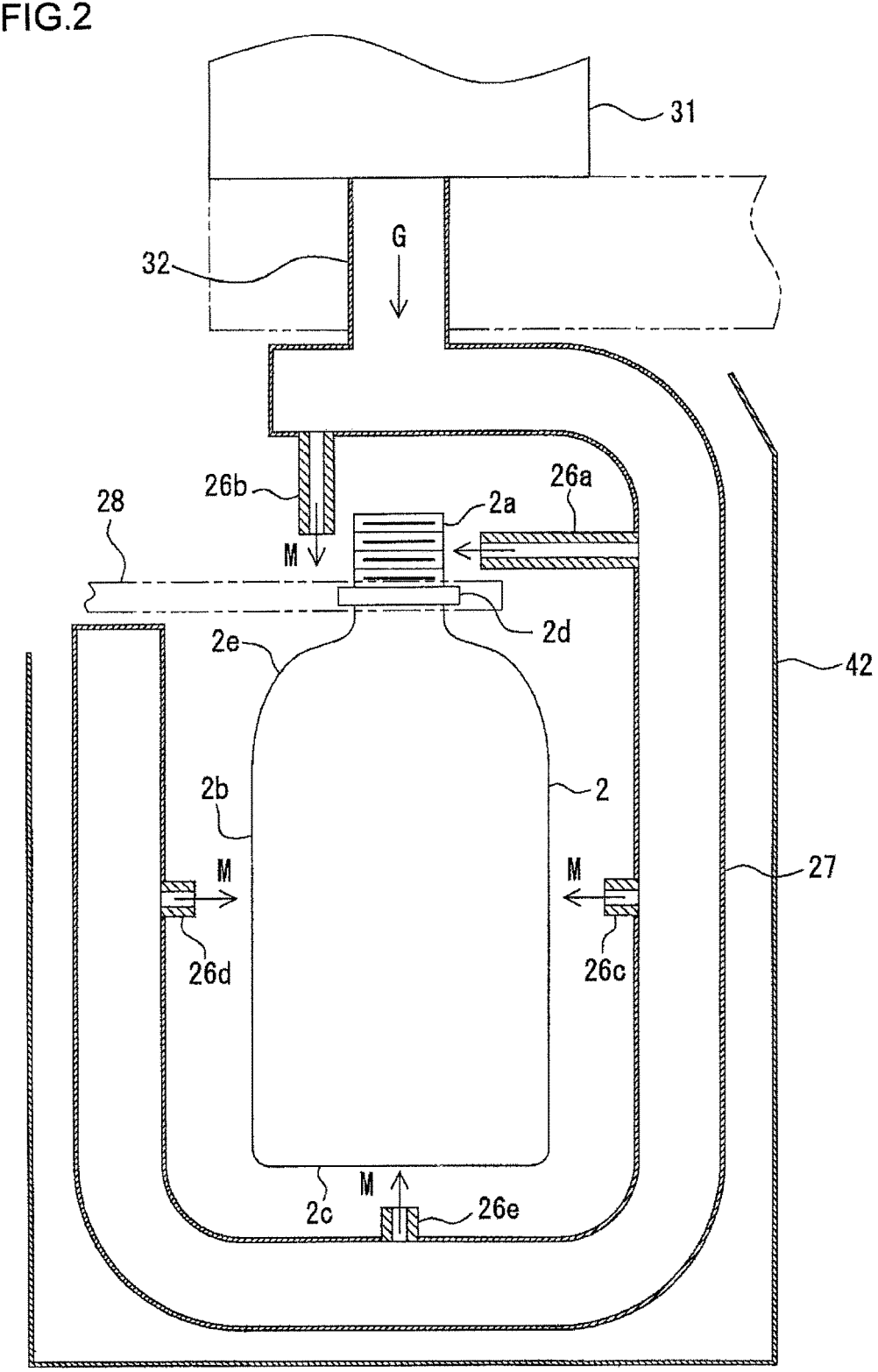
FIG. 2 is a vertical sectional view showing a sterilizer supplying section or unit.

A portion surrounding the wheel 25 is formed as a sterilizer supplying section 5 for applying the sterilizer to the outer surface of the bottle 2, and a plurality of nozzles 26a to 26e for the sterilizer (sterilizer nozzles) are arranged at predetermined portions around the wheel 25 as shown in FIGS. 1, 2 and 4(C).

These sterilizer nozzles 26a to 26e discharge the sterilizer toward the outer surface of the bottle 2 as a container to thereby apply the sterilizer onto the outer surface of the bottle 2, and the sterilizer nozzles 26a to 26e are arranged near the mouth portion 2a, a body portion 2b and the bottom portion 2c of the bottle 2, respectively. More specifically, a conduit 27 is disposed so as to extend in a manner of surrounding a contour of the bottle 2 on a horizontal plane including an axis of the bottle 2, and the sterilizer nozzles 26a to 26e are mounted to the conduit 27, so that the sterilizer introduced into the conduit 27 is discharged toward the outer surface of the bottle 2 through the respective nozzles 26a to 26e.

Herein, the bottle axis indicates herein an axis extending from the mouth portion 2a to the bottom portion 2c of the bottle 2 through the center thereof.

One sterilizer nozzle 26a among the plural sterilizer nozzles disposed near the mouth portion 2a of the bottle 2 is arranged in a manner such that the nozzle axis of the nozzle 26a is directed to intersect at right angle with the cylindrical wall portion of the mouth portion 2a, and another one sterilizer 26b is also arranged in a manner such that the nozzle axis of the nozzle 26b is directed to extend in parallel to a base line of the cylindrical wall portion along the outer surface thereof of the mouth portion 2a. The sterilizer, that is jetted from the sterilizer nozzle 26a arranged so that the nozzle axis thereof is directed to intersect at the right angle with the cylindrical wall portion of the mouth portion 2a, easily enters the threads of the male screw threads formed to the mouth portion 2a, and accordingly, the mouth portion 2a can be fairly sterilized. In addition, the sterilizer, that is jetted from the sterilizer nozzle 26b arranged in a manner such that the nozzle axis of the nozzle 26b is directed to extend in parallel to a base line of the cylindrical wall portion along the outer surface thereof of the mouth portion 2a, also easily reaches the support ring 2d formed to the base portion of the mouth portion 2a and a shoulder portion 2e formed between the mouth portion 2a and the body portion 2b, so that the outer surfaces of the support ring 2d and others can be also fairly sterilized.

At least a pair of sterilizer nozzles 26c and 26d are disposed near the body portion 2b of the bottle 2 so as to sandwich the body portion 2b from both the sides thereof. More preferably, the axis of each of the sterilizer nozzles 26c and 26d is disposed so as to intersect with the body portion 2b at the right angle. A plurality of these sterilizer nozzles 26c and 26d for blasting the sterilizer to the body portion 2b of the bottle 2 may be arranged along the vertical direction of the body portion 2b.

Further, at least one of the sterilizer nozzles 26e is disposed near the bottom portion 2c of the bottle 2. More preferably, it may be desired that the nozzle axis of the sterilizer nozzle 26e is disposed to intersect with the center portion of the bottom portion 2c at the right angle.

The conduit 27 extends vertically around the bottle 2 from the just above portion of the mouth portion 2a of the bottle 2 to the slightly lower portion of the support ring 2d so as to provide an approximately C-shape, and both the end portions of the conduit 27 are closed. As shown in FIG. 2, a portion between both ends of the C-shaped conduit 27 substantially corresponds to the support ring portion, so that the gripper 28 holding the bottle 2 at the support ring 2d can freely pass this portion without being interfered.

An evaporator (vaporizer) 29 for the sterilizer is connected to the conduit 27 as shown in FIG. 3.

In the present embodiment, hydrogen peroxide is used as such sterilizer.

This evaporator 29 is provided with a two-fluid spray-type hydrogen peroxide supply unit 30 for supplying drops of the sterilizer the hydrogen peroxide as the sterilizer and a heating pipe 31 for heating the sprayed hydrogen peroxide supplied from the hydrogen peroxide supply unit 30 to a temperature more than boiling point thereof and less than its undegradable temperature to thereby evaporate such hydrogen peroxide. The hydrogen peroxide supply unit 30 acts to spray the solution of the hydrogen peroxide into an evaporator chamber 31a of the heating pipe 31 by introducing the hydrogen peroxide solution and a compressed air from the hydrogen peroxide supply path 30a and the compressed air supply path 30b, respectively, into the evaporator chamber 31a. A heater 31b is interposed within the cylindrical wall portion of the heating pipe 31. The hydrogen peroxide spray blasted into the evaporator 31a is evaporated by the heating of the heater 31. The evaporated hydrogen peroxide gas G is guided into the conduit 27 through the pipe line 32, and then jetted as the hydrogen peroxide mist M from the sterilizer nozzles 26a to 26d toward respective portions of the bottle 2.

As shown in FIG. 1, the bottle 2 is conveyed around the wheel 25 in a state of being gripped by the gripper 28 (see FIG. 2) while being held thereby, and during this conveyance, the hydrogen peroxide gas G generated by the evaporator 29 is distributed to the respective sterilizer nozzles 26a to 26d through the pipe line 32 and the conduit 27, and the hydrogen peroxide mist M is thereafter jetted toward the outer surface of the bottle 2 from each of the sterilizer nozzles 26a to 26d. According to such operation, the thin film of the hydrogen peroxide adheres to the outer surface of the bottle 2.

Since the heat during the time from the preform heating process to the blow-molding process remains to the bottle 2, the sterilizing effect is achieved by the adhesion of the condensed hydrogen peroxide mist. In addition, by using such bottle 2 having the remaining heat, the heat transfer effect by the subsequent hot-water rinsing to be performed to the inner surface of the bottle, and the sterilizing effect to the bottle outer surface can be hence improved.

As shown in FIG. 2, in an area to which the sterilizer such as hydrogen peroxide is sprayed, the tunnel 42 may be located so as to be along the conveying direction of the bottle 2, in a location, such that the sterilizer mist M such as hydrogen peroxide or like stays within the tunnel 42, which efficiently condenses the sterilizer onto the surface of the bottle 2, thereby enhancing the sterilizing effect to the outer surface of the bottle 2.

The sterilizer supply section 5 is shielded from other portions or sections by the partition walls 10, 10a of the aseptic chamber 9. Although the hydrogen peroxide mist M fills in the sterilizer supply section 5, the surplus mist M is discharged outside the aseptic chamber 9 by discharge means, not shown.

As shown in FIG. 1, the hot-water rinsing section 6 is provided in adjacent to the downstream side portion of the sterilizer supply section 5.

Within the hot-water rinsing section 6, a wheel 34 for rinsing treatment is connected to the wheel 25 in the sterilizer supply section 5 through the intermediate wheel 33.

A gripper is provided for the hot-water rinsing wheel 34 to be capable of being vertically inverted with the moth portion 2a of the bottle 2 being gripped, though not shown, and as shown in FIG. 5(D), to be turnable with the inverted attitude being maintained.

A nozzle 35, as shown in FIG. 5(D), for the hot-water rinsing is mounted to the lower portion of each of the gripper to be vertically movable and also turnable synchronously with the gripper. As shown in FIG. 5(D), during the turning of the bottle 2, hot water w is jetted into the bottle 2 for a predetermined time interval from the hot-water supply nozzle 35.

Further, although the hot water w is supplied into the bottle 2 by inserting the hot water rinsing nozzle 35, as shown in FIG. 5(D), in a case where the hot-water rinsing nozzle 35 is not inserted into the bottle 2, the hot water w may be properly supplied into the bottle 2 by making thin the nozzle inner diameter of the hot water rinsing nozzle 35 to be 2 mm to 6 mm to thereby increasing the hot water feed pressure to be more than 0.2 MPa.

It is further preferred that the temperature of the hot water w supplied into the bottle 2 from the how water rinsing nozzle 35 is of 65° C. to 90° C., the flow rate thereof is 5 L/min/ to 15 L/min per one hot water rinsing nozzle 35, and the hot water supplying time is of 0.2 to 20 sec.

Furthermore, in order to enhance the sterilizing effect and the foreign substance removing effect, it may be preferred to vibrate the bottle at least more than one time, and by vibrating the bottle 2, the amount of the hot water to be used will be reduced. The vibration of the bottle 2 will be performed by contacting the gripper 24, which travels with the bottle being held, to a cam, for example, not shown, and then swinging the gripper 24 vertically or laterally.

According to the process mentioned above, the inner surface of the bottle 2 is sterilized by the heat of the hot water. Further, the hydrogen peroxide, which may slightly enter the interior of the bottle 2, is flowed out of the bottle 2, and in addition to no use of the sterilizer such as hydrogen peroxide for the sterilization of the interior of the bottle 2, the sterilizer such as the hydrogen peroxide can be completely prevented from remaining inside the bottle 2. Moreover, the sterilizing effect to the outer surface of the bottle 2 can be enhanced by activating the hydrogen peroxide adhering to the outer surface of the bottle 2 by the heat transferred from the hot water w in the bottle 2.

A large amount of water steam and condensed water is produced in the chamber of the hot-water rinsing section 6. As shown in FIG. 1, the aseptic air which is sterilized by the HEPA filter 43 is always supplied into the filling section 7, and accordingly, the pressure inside the filling section 7 becomes positive more than that in the hot-water rinsing section 6 and the steam easily enters the chamber of the sterilizer supplying section 5 from the chamber of the how-water rinsing section 6. However, the sterilizing effect can be highly maintained in a state in which the interior of the chamber of the sterilizer supplying section 5 is dried. Then, as shown in FIG. 1, in order to prevent the steam from entering the chamber of the sterilizer supplying section 5, it is preferred to provide exhaust means, not shown, in the chambers of the hot-water rinsing section 6 and the sterilizer supplying section 5.

After the sterilizing and the rinsing by the hot water w, the bottle 2 is again inverted into the normal standing position by the gripper and conveyed to the succeeding filling section 7.

As shown in FIG. 1, the filling section 7 is provided on the downstream side of the hot-water rinsing section 6.

A wheel 37 for the filler connected to the wheel 34 for the hot-water rinsing treatment via the intermediate wheel 36 is provided in the filling section 7 as bottle conveying means.

Below each of the grippers in the wheel 37 for the filler, a drink filling nozzle 38 such as shown in FIG. 5(E) is disposed to be synchronously turnable for each of the grippers. As shown in FIG. 5(E), during the turning motion of the bottle 2, the drink filling nozzle 38 fills the bottle 2 with the drink d by a predetermined amount. As the drink d for filling the bottle 2, mineral water, carbonated drink or other some functional drinks which has a nature difficult to decompose a sterilizer such as hydrogen peroxide will be selected.

As shown in FIG. 1, a wheel 40 for the capper is connected to the downstream side portion of the wheel 37 for the filler through the intermediate wheel 39.

A capper for the wheel 40 for the capper is provided for each gripper. The capper applies the cap 17 by screwing it to the mouth portion 2a of the bottle 2 in which the drink d is filled, as shown in FIG. 5(F), and the bottle is then sealed. Accordingly, the drink filled product of the bottle 2 is completed.

The drink filled product is conveyed out of the aseptic chamber by the conveying wheel disposed in adjacent to the wheel 40 for the capper.

Further, the cap 17 is preliminarily sterilized by the mist of the sterilizer such as hydrogen peroxide or like before the application to the bottle 2 by the capper. More specifically, as like as the case of the bottle 2, after the hydrogen peroxide mist or gas is sprayed to the inner and outer surfaces, these surfaces are dried by the hot air, thereby performing the sterilizing treatment. The thus sterilized cap 17 is conveyed within a chute held in aseptic condition, not shown, to the capper 17, and thereafter, the cap 17 is screwed with the mouth portion 2a to fasten and seal the mouth portion 2a.

Since the cap 17 is made of polyethylene or polypropylene, the cap 17 has less hydrogen peroxide adsorption ability in comparison with the PET as a material for the bottle 2, and accordingly, no sterilizer (particularly, hydrogen peroxide) remains to the cap 17 after being sterilized.

As described above, as to the sterilization to the bottle 2 and the cap 17, the outer surface, other than the inner surface, of the bottle 2 and the inner and outer surface of the cap 17 are sterilized by the sterilizer, and only the inner surface of the bottle 2 is sterilized by the hot-water w, so that the sterilizer does not remain substantially completely in the drink filled product. In addition, since the hot-water w is used only for the inner surface of the bottle 2, the amount of the water to be used can be minimally reduced, and moreover, when the interior of the bottle 2 is sterilized by the hot-water w, foreign material or substance, which may remain inside the preform 1, can be flowed out of the bottle 2 by the hot-water w.

In the following, the function of the aseptic filling system of the structure mentioned above will be described in consideration of the function of the bottle sterilizing device and the bottle sterilizing method.

As shown in FIG. 1, at first, the preform 1 is conveyed into the heating section 3 by the conveying chute 12 of the preform supply machine 11.

When the preform 1 is guided into the preform heating section 3, the preform 1 is held by the holding member 15 mounted to the endless chain 14, and then, as shown in FIG. 1 and FIG. 4(A), the preform 1 is heated by the heater 16 to the temperature suitable for the blow-molding treatment while travelling together with the endless chain 14.

The preform 1 heated to the predetermined temperature is transferred to the molding section 4 through the holding member 15 of the endless chain 14 and the wheels 18, 19 of the gripper, and thereafter, received by the blow-molding mold 20 turning together with the wheel 19 as shown in FIG. 4(B).

When the blow-molding mold 20 receives the preform 1 and is then closed, the extension rod 22 is lowered from the valve block 21 provided for the upper portion of the blow-molding mold 20 toward the bottom of the interior of the preform 1 to thereby expand the preform 1. Thereafter, the blowing-air is blasted into the preform 1 from the valve block 21, and the preform 1 is molded into the bottle 2 in the cavity C of the blow-molding mold 20.

The blow-molding mold 20 is turned together with the wheel 19, and when the mold 20 contacts the wheel 23 for conveyance, the mold 20 is opened, and the molded bottle 2 is transferred to the gripper, not shown, of the conveying wheel 23.

The bottle 2, for example, the end face of the mouth portion 2a thereof, is photographed by the inspection camera at a time of turning around the conveyance wheel 23 to thereby inspect and discriminate the condition of smoothness of the end face, and in this inspection, when the smoothness of the end face is discriminated not to be good, i.e., to be defective, such bottle 2 is rejected out of the conveying path by the rejecting device, not shown.

The bottle 2 discriminated to be good is conveyed to the sterilizer supplying section 5, and as shown in FIG. 2 and FIG. 4(C), passes the space surrounded by the conduit 27.

The sterilizer gas G such as hydrogen peroxide gas evaporated by the evaporator 29 shown in FIG. 3 flows into the conduit 27, and such gas G is discharged as the sterilizer mist M through each of the sterilizer nozzles 26a to 26d.

Accordingly, when the bottle 2 passes the portion surrounded by the conduit 27, the sterilizer mist M is blasted to the outer surface of the bottle 2 from each of the plural sterilizer nozzles 26a to 26d mounted to the conduit 27.

Since the sterilizer nozzles 26a to 26d are arranged so that the respective axes of these nozzles do not intersect with the openings of the mouth portions 2a of the bottles 2, and accordingly, the sterilizer mist M is blasted toward the outer surface of the mouth portion 2a of the bottle 2, the outer surface of the body portion thereof and the outer surface of the bottom portion thereof without directing toward the interiors of the bottles 2 through the mouth portions 2*a*. Thus, the film having thin thickness of the hydrogen peroxide as the sterilizer can evenly adheres to the outer surface of each bottle 2.

One sterilizer nozzle 26*a* among the plural sterilizer nozzles 26*a* to 26*d* is arranged in a manner such that the nozzle axis of this nozzle is directed to intersect at right angle with the cylindrical wall portion of the mouth portion 2*a* of the bottle 2, and hence, the sterilizer mist M jetted from this sterilizer nozzle 26*a* easily enters the threads of the male screw threads formed to the mouth portion 2*a*. Thus, the outer surface of the mouth portion 2*a* can be fairly sterilized.

In addition, since the other one sterilizer nozzle 26*b* is arranged in a manner such that the nozzle axis of the nozzle 26*b* is directed to extend in parallel to a base line of the cylindrical wall portion along the outer surface thereof of the mouth portion 2*a*, the sterilizer mist M jetted from this sterilizer nozzle 26*b* also easily reaches the support ring formed to the base portion of the mouth portion 2*a* and a shoulder portion 2*e* formed between the mouth portion 2*a* and the body portion 2*b*, so that the outer surfaces of these portions can be also fairly sterilized.

The bottle 2 having the outer surface on which the sterilizer is applied is conveyed to the hot-water rinsing section 6 as shown in FIG. 1 and FIG. 5(D).

In the hot-water rinsing section 6, the bottle 2 is inverted in its vertical attitude, and the hot water w is supplied into the bottle 2 from the mouth portion 2*a* directed downward. Although the hot-water supplying nozzle 35 remains outside of the bottle 2 in the illustrated example, it may be possible to supply the hot water w into the bottle 2 while being inserted therein.

The inner surface of the bottle 2 is subjected to the sterilizing treatment by the heat of the hot water w. In addition, the hydrogen peroxide as the sterilizer, which might enter, even slightly, the bottle 2 in the sterilizer supplying section 5, flows out of the bottle 2, thus preventing the hydrogen peroxide from remaining in the bottle 2. Furthermore, the hydrogen peroxide as the sterilizer adhering to the outer surface of the bottle 2 is activated by the heat transferred from the hot water w in the bottle 2, and hence, the sterilizing effect to the outer surface of the bottle 2 can be enhanced.

After discharging the hot water w out of the bottle 2, the bottle 2 is again turned in the normal attitude, and as shown in FIG. 1, the bottle 2 is conveyed to the next filling section 7.

As shown in FIG. 5(E), in the filling section 7, the drink d fills the bottle 2 by a predetermined amount from the drink filling nozzle 38. The drink d filling the bottle 2, such as mineral water, carbonated drink or the like, has a nature difficult to decompose the sterilizer such as hydrogen peroxide.

Subsequently, as shown in FIG. 5(E), in the filling section 7, the cap 17 is screwed to the mouth portion 2*a* of the bottle 2 in which the drink d is filled to be sealed.

According to such operation as described above, the bottle 2 as the drink filled product 2 is completed, which is then discharged out of the aseptic chamber 9.

Second Embodiment

Figure 6:
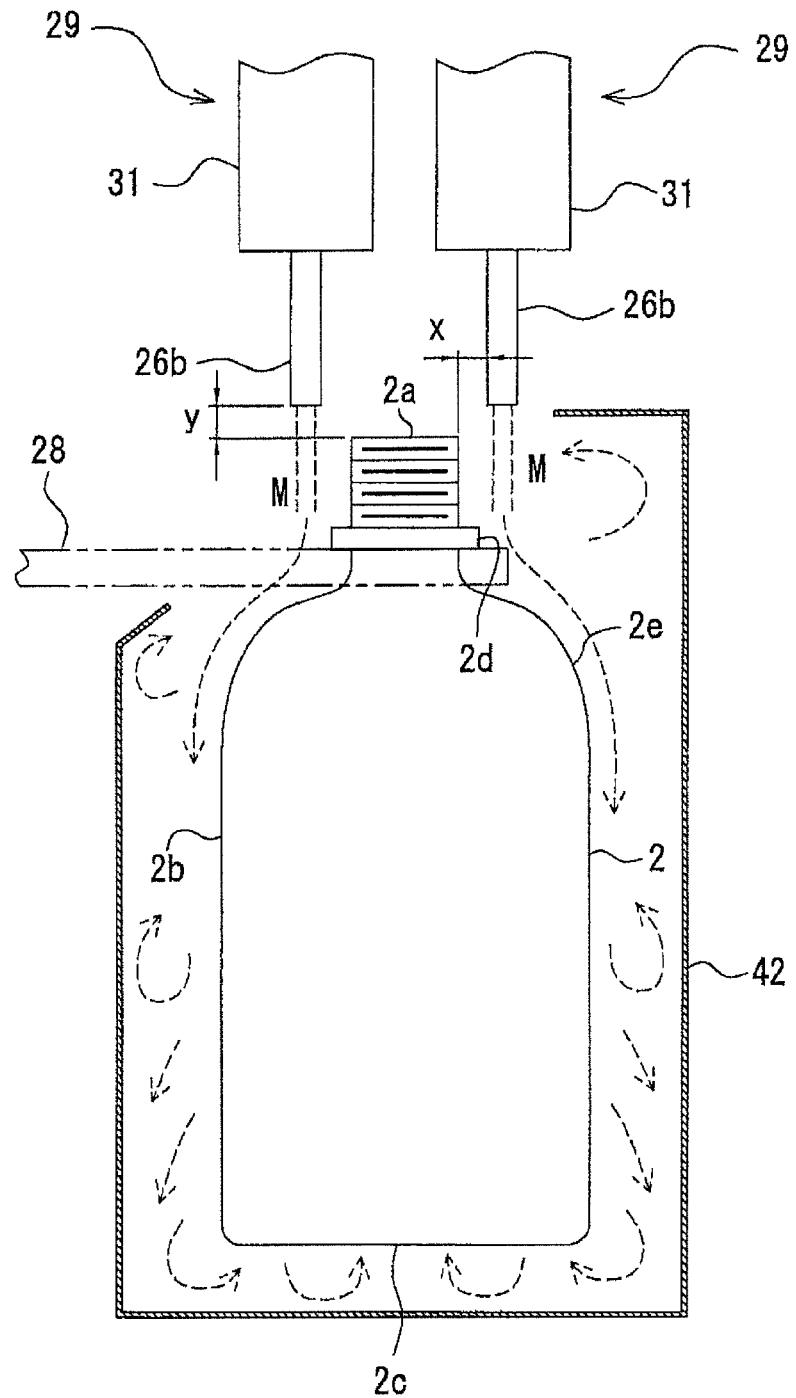
FIG. 6 is a front view of another embodiment of a sterilizer supplying section as viewed from a container travelling direction.

In this second embodiment, as shown in FIG. 6, at least a pair of nozzles 26*b* for the sterilizer each corresponding to the sterilizer nozzle 26*b* in the first embodiment are disposed so as to sandwich the mouth portion 2*a* of the bottle 2. The paired nozzles 26*b* are arranged at positions at which the paired nozzles 26*b* do not contact the mouth portion 2*a* of the bottle 2 to be conveyed and the sterilizer discharged from the sterilizer nozzles 26*b* does not enter into the bottle 2 through the mouth portion 2*a*.

More specifically, it is desirable that the distance y between the tip end of the sterilizer nozzle 26*b* and the ceiling surface as horizontal surface of the mouth portion 2*a* of the bottle 2 is set to be within 0 mm to 30 mm. In a case where the tip end of the sterilizer nozzle 26*b* is not more than 0 mm, that is, the tip end thereof is positioned below the ceiling surface, it becomes difficult for the hydrogen peroxide to adhere to the ceiling surface of the mouth portion 2*a* or near, particularly, to the male screw thread portion, which may result in defective sterilization. On the other hand, in a case where the distance y is not less than 30 mm, that is, where the tip end of the sterilizer nozzle 26*b* is apart by 30 mm from the ceiling surface of the mouth portion 2*a*, the hydrogen peroxide will easily enter the bottle 2.

Further, it is also desirable that the distance x between the side surface of the sterilizer nozzle 26*b* and the side surface of the mouth portion 2*a* of the bottle 2 is set to be within 0 mm to 20 mm. In a case where the distance x is not more than 0 mm, that is, where the sterilizer nozzle 26*b* positioned inside the side surface of the mouth portion 2*a*, the hydrogen peroxide will easily enter the bottle 2. On the other hand, in a case where the distance x is not less than 20 mm, it becomes difficult for the hydrogen peroxide to adhere to the outer surface of the mouth portion 2*a*, which may result in defective sterilization to the mouth portion 2*a* and so on.

Further, it may be desired that the inner diameter of the sterilizer nozzle 26*b* is within 2 mmΦ to 10 mmΦ.

An evaporator 29 such as shown in FIG. 3 is provided on the upstream side of each of the sterilizer nozzles 26*b*.

The gas of the sterilizer such as hydrogen peroxide flows into the sterilizer nozzle 26*b* from the heating pipe 31, and the gas is converted into mist M which is then jetted out from the tip end of the sterilizer nozzle 26*b*. The mist M to be jetted from the tip end of the sterilizer nozzle 26*b* is blasted as shown with broken line in FIG. 6 at the pressure of 0.5 MPa, for example, and flows along the outer surface of the body portion 2*b* and the bottom portion 2*c* of the bottle 2 from the outer surface of the shoulder portion 2*e* of the bottle 2 without flowing into the male screw thread and the support ring 2*d* as the outer surface of the mouth portion 2*a* of the bottle 2. According to such flow of the mist M, the outer surface of the bottle 2 can be properly sterilized.

As shown in FIG. 6, it may be possible to provide a tunnel 42 in an area into which the sterilizer such as hydrogen peroxide is jetted so as to extend along the bottle conveying direction. In such arrangement, the mist M of the sterilizer such as hydrogen peroxide can be effectively condensed on the surface of the bottle 2 by staying in the tunnel 42, thereby enhancing the sterilizer effect to the outer surface of the bottle 2.

Third Embodiment

Figure 7:
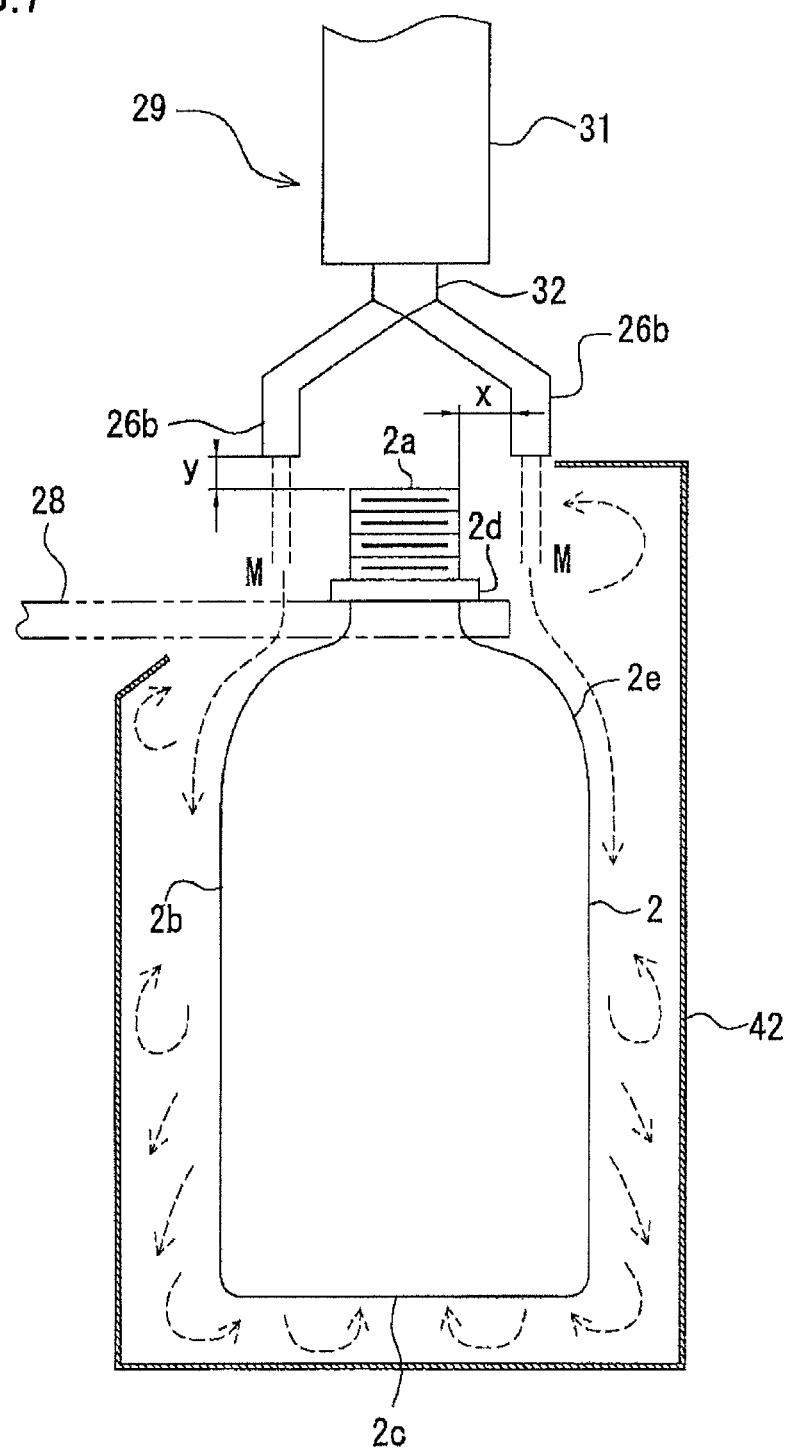
FIG. 7 is a front view of a further embodiment of a sterilizer supplying section as viewed from a container travelling direction.

In this third embodiment, as shown in FIG. 7, the sterilizer nozzles 26*b* are arranged so as to sandwich the mouth portion 2*a* of the bottle 1 within a plane perpendicular to the bottle conveying direction, as like as in the second embodiment.

However, one evaporator 29 for the sterilizer, such as shown in FIG. 3, is arranged on the upstream side of the both the lateral sterilizer nozzles 26*b*. This one evaporator 29 is provided with the pipe line 32 for discharging the hydrogen peroxide gas G, from which the lateral sterilizer nozzles 26b are branched.

In this third embodiment, both the lateral sterilizer nozzles 26b are disposed with the distances x and y as described for the second embodiment.

The gas of the sterilizer such as hydrogen peroxide generated in the evaporator 29 flows into each of the sterilizer nozzles 26b from the pipe line 32 from the heating pipe 31, and the gas is converted into mist M which is then jetted out from the tip end of the sterilizer nozzle 26b. The mist M jetted from the tip end of the sterilizer nozzle 26b flows along the outer surface of the bottle 2 without flowing into the bottle 2, reaches the support ring 2d provided at the lower side of the mouth portion 2a of the bottle 2 and the shoulder portion 2e between the mouth portion 2a and the body portion 2b, and then reaches the body portion 2b and the bottom portion 2c, thus properly sterilizing the outer surface of the bottle 2.

In this third embodiment, as shown in FIG. 7, it may be possible, as in the second embodiment, to provide a tunnel 42 in an area into which the sterilizer such as hydrogen peroxide is jetted so as to extend along the bottle conveying direction.

It is further to be noted that the present invention is not limited to the above embodiments, and although, in the described embodiments, the hydrogen peroxide is used as sterilizer, any substance for the sterilizer which includes hydrogen peroxide component of not less than 1% may be usable even a drug product of peracetic acid.

Furthermore, in the above embodiments, although the sterilization of the container is performed by two processes including the sterilizing process using the sterilizer such as hydrogen peroxide and the hot-water rinsing process, a hot-air rinsing process may be added before the hot-water rinsing process.

Still furthermore, in the case where the male screw thread portion formed in the outer surface of the mouth portion is not sufficiently sterilized by jetting the sterilizer, for example, that portion may be sterilized by spraying the hot-water at the same time performing the hot-water rinsing process made to the inner surface of the container.

Still furthermore, the sterilizer nozzles shown in FIGS. 2, 4, 6 and 7 may be used alone as single nozzle, respectively, in accordance with the shape of a container, ability of a filling machine, or it may be possible to use them in combination. Furthermore, each of these sterilizer nozzles may be arranged in parallel to the outer surface of the mouth portion of the container and the body portion thereof, or arranged perpendicularly thereto, otherwise, they may be arranged obliquely with an angle at which the sterilizer does not enter the container.

Still furthermore, in a case when bacteria contamination degree at the initial time of the preform exceeds 1%, the preform may be preliminarily sterilized by a sterilizing device, not shown, for the preform, and thereafter, the sterilizing processes mentioned above may be performed to the bottle.

REFERENCE NUMERAL

2—container (bottle), 2a—mouth portion, 2b—body portion, 2c—bottom portion, 26a to 26d—sterilizer nozzle, 27—conduit, 35—hot-water nozzle, G—gas, w—hot-water.

The invention claimed is:

1. A method of sterilizing a container, wherein a sterilizer is applied to an outer surface of a container having a mouth portion, by blasting the sterilizer toward the outer surface of the container from at least one first sterilizer nozzle for applying the sterilizer disposed such that the sterilizer does not enter into the container through the mouth portion and so as not to intersect with the mouth portion of the container, wherein the first sterilizer nozzle is provided so as to extend along the outer surface of a cylindrical wall portion of the mouth portion of the container, such that the sterilizer jetted from the first sterilizer nozzle reaches a support ring formed in a base portion of the mouth portion and a shoulder portion formed between the mouth portion and a body portion of the container,
  wherein at least one second sterilizer nozzle is provided so as to intersect with the cylindrical wall portion of the mouth portion of the container, such that the sterilizer jetted from the second sterilizer nozzle enters threads of a male screw thread formed around the mouth portion, and
  wherein the sterilizer is not provided within an inner surface of the container and the inner surface of the container is sterilized by only hot-water supplied into the container from a nozzle for hot-water, and the sterilizer adhering to the outer surface of the container is activated by heat transferred from the hot-water to thereby sterilize the outer surface of the container.

2. The container sterilizing method according to claim 1, wherein a conduit is arranged so as to extend to surround a contour of the container in a flat plane including an axis of the container, with the conduit provided in an approximately C-shape, and the first sterilizer nozzle is provided for the conduit in a manner such that the sterilizer introduced into the conduit is discharged toward the mouth portion, body portion and bottom portion of the container from the first sterilizer nozzle.

3. The container sterilizing method according to claim 1, wherein the sterilizer is blasted to the container to which heat at a time of molding process remains.

4. An apparatus for sterilizing a container comprising: a conveying means for conveying a container having a mouth portion; at least one first sterilizer nozzle for applying a sterilizer to an outer surface of the container from an upstream side to a downstream side with respect to the conveying means, the first sterilizer nozzle being disposed such that the sterilizer does not enter into the container through the mouth portion, wherein the first sterilizer nozzle is provided so as to extend along the outer surface of a cylindrical wall portion of the mouth portion of the container, such that the sterilizer jetted from the first sterilizer nozzle reaches a support ring in a base portion of the mouth portion and a shoulder portion formed between the mouth portion and a body portion of the container;
  at least one second sterilizer nozzle that is provided so as to intersect with the cylindrical wall portion of the mouth portion of the container, wherein the sterilizer jetted from the second sterilizer nozzle enters threads of a male screw thread formed around the mouth portion;
  a fluid of only hot-water; a nozzle for supplying only the hot-water into the container, wherein the inner surface of the container is sterilized by only the hot-water supplied into the container from the nozzle for supplying only the hot-water, and the sterilizer adhering to the outer surface of the container is activated with heat transferred from only the hot-water to thereby sterilize the outer surface of the container; and
  wherein the apparatus does not include a nozzle for supplying a fluid into the container between the first and second sterilizer nozzles and the nozzle for supplying only the hot-water, and the apparatus does not include a nozzle for rinsing subsequent to the nozzle for supplying only the hot-water.

5. The container sterilizing apparatus according to claim 4, wherein a conduit is arranged so as to extend to surround a contour of the container in a flat plane including an axis of the container, with the conduit provided in an approximately C-shape, and the first sterilizer nozzle is provided for the conduit in a manner such that the sterilizer introduced into the conduit is discharged toward the mouth portion, body portion and bottom portion of the container from the first sterilizer nozzle.

6. The container sterilizing apparatus according to claim 4, wherein the sterilizer is blasted to the container to which heat at a time of molding process remains.

7. The container sterilizing apparatus according to claim 4, wherein the first sterilizer nozzle is at least a pair of first sterilizer nozzles for applying the sterilizer disposed so as to sandwich the mouth portion of the container, wherein a distance between a tip end of each first sterilizer nozzle and a horizontal ceiling surface of the mouth portion of the container is set to be within 0 mm to 30 mm, and a distance between a side surface of each first sterilizer nozzle and a side surface of the mouth portion of the container is set to be within 0 mm to 20 mm.

* * * * *